US008940697B2

(12) United States Patent (10) Patent No.: US 8,940,697 B2
Podgoreanu et al. (45) Date of Patent: Jan. 27, 2015

(54) COMPOSITIONS AND METHODS FOR THE TREATMENT OF MYOCARDIAL ISCHEMIA/REPERFUSION INJURY WITH ANNEXIN A1 SHORT PEPTIDE

(75) Inventors: Mihai V. Podgoreanu, Chapel Hill, NC (US); Zhiquan Zhang, Durham, NC (US); Qing Ma, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 13/502,219

(22) PCT Filed: Oct. 15, 2010

(86) PCT No.: PCT/US2010/052884
§ 371 (c)(1),
(2), (4) Date: Jul. 2, 2012

(87) PCT Pub. No.: WO2011/047290
PCT Pub. Date: Apr. 21, 2011

(65) Prior Publication Data
US 2012/0270790 A1    Oct. 25, 2012

Related U.S. Application Data

(60) Provisional application No. 61/279,120, filed on Oct. 16, 2009.

(51) Int. Cl.
*A61K 38/06* (2006.01)
*C07K 5/08* (2006.01)
*A61P 9/10* (2006.01)
*A61K 38/17* (2006.01)

(52) U.S. Cl.
CPC .................................. *A61K 38/1709* (2013.01)
USPC ........................ 514/16.4; 530/331; 514/21.9

(58) Field of Classification Search
CPC ..... A61K 38/06; A61K 38/1709; C07K 5/08; C07K 5/0802
See application file for complete search history.

(56) References Cited

U.S. PATENT DOCUMENTS

2003/0171297 A1    9/2003    Perritti et al.
2012/0004175 A1    1/2012    Zhang et al.

FOREIGN PATENT DOCUMENTS

WO    WO 2008/121881 A2 *    10/2008    ............. A61K 38/00

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BloL (2002) 324, 373-386.*
Valen et al, Nuclear Factor Kappa-B and the Heart, Journal of the American College of Cardiology, 2001, 38, pp. 307-314.*
Su et al, Acute hyperglycemia exacerbates myocardial ischemia/reperfusion injury and blunts cardioprotective effect of GIK, Am J Physiol Endocrinol Metab, 2007, 293, pp. E629-E635.*
Parikh et al, Urinary IL-18 is an early predictive biomarker of acute kidney injury after cardiac surgery, Kidney International, 2006, 70, pp. 199-203.*
Zhai et al, Effect of estrogen on global myocardial ischemiareperfusion injury in female rats, Am J Physiol Heart Circ Physiol, 2000, 279, pp. H2766-H2775.*
Pelzer et al, 17b-Estradiol Prevents Programmed Cell Death in Cardiac Myocytes, Biochemical and Biophysical Research Communications, 2000, 268, pp. 192-200.*
Meldrum et al, Intracellular Signaling Mechanisms of Sex Hormones in Acute Myocardial Inflammation and Injury, Frontiers in Bioscience, 2005, 10, pp. 1835-1867.*
Bizzarro et al. "Annexin A1 N-Terminal Derived Peptide Ac2-26 Stimulates Fibroblast Migration in High Glucose Conditions" *PLOS One*, 7(9): e45639 (2012).
Ernst et al. "An annexin 1 N-terminal peptide activates leukocytes by triggering different members of the formyl peptide receptor family" *J. Immunol* 172:7669-7676 (2004).
Gastardelo et al. "Functional and Ultrastructural Analysis of Annexin A1 and Its Receptor in Extravasating Neutrophils during Acute Inflammation" *The American Journal of Pathology*, 174(1):177-183 (2009).
Gavins et al. "Annexin 1 and Melanocortin Peptide Therapy for Protection Against Ischaemic-Reperfusion Damage in the Heart" *The Scientific World Journal*, 6:1008-1023 (2006).
Gavins et al. "Activation of the annexin 1 counter-regulatory circuit affords protection in the mouse brain microcirculation" *The FASEB Journa*, 21:1751-1758 (2007).
Hayhoe et al. "Annexin 1 and its bioactive peptide inhibit neutrophil-endothelium interactions under flow: indication of distinct receptor involvement" *Blood*, 107:2123-2130 (online publication Nov. 8, 2005).
Hoffman and Linderman "Receptor up-regulation, internalization, and interconverting receptor states" *J Biol Chem*, 271(31):18394-404 (1996).
Kamal et al. "An annexin 1 (ANXA1)-derived peptide inhibits prototype antigen-driven human T cell Th1 and Th2 responses in vitro" *Clin Exp Allergy*, 31:1116-1125 (2001).
Kosicka-Knox et al. "Ac 2-26, an annexin A1-derived peptide, reduces inflammation in human SGBS adipocytes after hypoxia treatment" *Endocrine Abstracts*, 29:P1172 (2012) (Abstract).
La et al. "Annexin 1 peptides protect against experimental myocardial ischemia-reperfusion: analysis of their mechanism of action" *The FASEB Journal*, 15:2247-2256 (2001).

(Continued)

*Primary Examiner* — Julie Ha
*Assistant Examiner* — Li Ni Komatsu
(74) *Attorney, Agent, or Firm* — Myers Bigel Sibley & Sajovec, P.A.

(57) ABSTRACT

The present invention provides a method of treating, ameliorating or preventing myocardial ischemia/reperfusion injury in a subject in need thereof, by administering to the subject a therapeutically effective amount of an annexin A1 short peptide (ANXA1sp).

3 Claims, 11 Drawing Sheets

(56) References Cited

OTHER PUBLICATIONS

Leoni et al. "Annexin A1, formyl peptide receptor, and NOX1 orchestrate epithelial repair" *The Journal of Clinical Investigation*, 123(1):443-454 (2013).

Perretti et al. "Annexin 1: An Endogenous Anti-Inflammatory Protein" *Physiology*, 18:60-64 (2003).

Perretti et al. "Involvement of the receptor for formylated peptides in the in vivo anti-migratory actions of Annexin 1 and its mimetics" *Am J Pathol* 158(6):1969-1973 (2001).

Ritchie et al. "Annexin-1 peptide $Anx_{12-26}$ protects adult rat cardiac myocytes from cellular injury induced by simulated ischaemia" *British J Pharmacol* 145:495-502 (2005).

Ritchie et al. "Cardioprotective actions of an N-terminal fragment of annexin-1 in rat myocardium in vitro" *Eur J Pharmacol* 461(2-3):171-179 (2003).

Qing et al. "Novel Annexin A1 Tripeptide Ameliorates Acute Kidney Injury after Deep Hypothermic Circulatory Arrest" *ASA Abstracts*, Oct. 16, 2010 (Abstract A092)).

Zhang et al. "A Novel Annexin A1 Peptide Attenuates Perioperative Myocardial Injury Exacerbated by Hyperglycemia" *ASA Abstracts*, Oct. 19, 2009 (Abstract A765)).

Zhang et al. "Abstract 3007: Annexin-A1 Mimetic Peptide and PPAR-alpha Agonist Attenuate Hyperglycemic Exacerbation of Myocardial Ischemia/Reperfusion Injury Following Cardioplegic Arrest in the Rat" *Circulation*, 120(18 Supplemental):S731, Nov. 3, 2009 (Abstract).

La et al. "Annexin 1 Peptides Protect Against Experimental Myocardial Ischemia-Reperfusion: Analysis of Their Mechanism of Action" *FASEB Journal* 15:2247-2256 (2001).

International Search Report and Written Opinion dated Jan. 10, 2011 for International Application No. PCT/US2010/052884 (12 pages).

International Preliminary Report on Patentability dated Apr. 26, 2012 for International Application No. PCT/US2010/052884 (9 pages).

\* cited by examiner

1. Ac-QAW
2. Ac-KQAW (SEQ ID NO:3)
3. AcAMVSEFLKQAWFIENIIQEYVQTVK (SEQ ID NO:10)
4. Ac-FLK
5. Ac-EFLKQAW (SEQ ID NO:6)
6. Ac-VSEFLKQAW (SEQ ID NO:9)

COMPOSITIONS AND METHODS FOR THE TREATMENT OF MYOCARDIAL ISCHEMIA/REPERFUSION INJURY WITH ANNEXIN A1 SHORT PEPTIDE

STATEMENT OF PRIORITY

The present invention is a 35 U.S.C. §371 national phase application of International Application Serial No. PCT/US2010/052884, filed Oct. 15, 2010, which claims the benefit, under 35 U.S.C. §119(e), of U.S. Provisional Application No. 61/279,120, filed Oct. 16, 2009, the entire contents of each of which are incorporated by reference herein.

STATEMENT OF GOVERNMENT SUPPORT

This invention was made with government support under Grant No. HL092071 awarded by the National Institutes of Health. The government has certain rights in the invention.

FIELD OF THE INVENTION

The present invention relates to compositions and methods for the treatment of myocardial ischemia/reperfusion injury using Annexin AI (ANXA1)-related peptides.

BACKGROUND OF THE INVENTION

Perioperative myocardial injury (PMI) secondary to ischemia/reperfusion (I/R) remains a major cause of cardiovascular morbidity and mortality following cardiac surgery and transplantation, and is further exacerbated by acute hyperglycemia. Hyperglycemic exacerbation of PMI significantly blocks the cardioprotective effect afforded by glucose-insulin-potassium (GIK). To date, there is not an effective treatment or prevention of perioperative myocardial injury due to ischemia/reperfusion.

Annexin A1 (ANXA1), a 37 kDa protein, is a member of the annexin superfamily, which consists of 13 calcium and phospholipid binding proteins with a significant degree of biological and structural homology (40-60%). ANXA1, originally identified as a mediator of the anti-inflammatory effects of glucocorticoids, has diverse biological functions including the regulation of inflammatory pathways, cell proliferation machinery, cell death signaling, and the process of carcinogenesis. Altering the expression or the localization of this protein can contribute to the pathogenesis of human diseases including inflammatory diseases, cardiovascular diseases and cancer. It has been demonstrated that ANXA1 reduces the leukocyte-dependent myocardial damage associated with myocardial I/R injury (La et al. (2001) *FASEB J.* 15(12):2247-2256). The functional link between migrated leukocytes and the myocardial damage was confirmed, and significantly lower numbers of extravasated leukocytes were counted in the group of rats treated with ANXA1 (La, M. et al. supra).

Pharmacological analysis has also demonstrated that the first 25 amino acids of the N-terminus of ANXA1 (termed Ac2-26) is the active region of biological function and can reproduce the anti-inflammatory actions of the full-length protein. Ac2-26 protects against splanchnic artery occlusion and reperfusion injury by affecting neutrophil migration and against experimental myocardial ischemia-reperfusion by attenuating neutrophil migration (Gasterdelo et al. (2009) *Am. J. Pathol.* 174(1):177-183).

Therefore, it is an object of the present invention to provide new compositions comprising ANXA1, and methods of using such compositions, to address this unmet need.

SUMMARY OF THE INVENTION

In one aspect, the present invention provides a method of treating myocardial ischemia/reperfusion injury in a subject in need thereof, comprising, consisting essentially of or consisting of administering to the subject a therapeutically effective amount of an ANXA1sp (Ac-QAW) peptide.

In another aspect, the present invention provides a method of ameliorating myocardial ischemia/reperfusion injury in a subject in need thereof, comprising, consisting essentially of or consisting of administering to the subject a therapeutically effective amount of an ANXA1sp peptide.

In a further aspect, the present invention provides a method of preventing myocardial ischemia/reperfusion injury in a subject in need thereof, comprising, consisting essentially of or consisting of administering to the subject a therapeutically effective amount of an ANXA1sp peptide.

Additional aspects of this invention include a kit for the treatment, amelioration and/or prevention of myocardial ischemia/reperfusion injury in a subject in need thereof, comprising an ANXA1sp peptide and instructions for use in the treatment, amelioration and/or prevention of myocardial ischemia/reperfusion injury in a subject in need thereof.

Further aspects include the use of an ANXA1sp peptide in the manufacture of a medicament for the treatment of myocardial ischemia/reperfusion injury in a subject in need thereof.

Additionally provided herein is the use of an ANXA1sp peptide in the manufacture of a medicament for the amelioration of myocardial ischemia/reperfusion injury in a subject in need thereof.

Also provided herein is the use of an ANXA1sp peptide in the manufacture of a medicament for the prevention of myocardial ischemia/reperfusion injury in a subject in need thereof.

BRIEF DESCRIPTION OF THE DRAWINGS

The foregoing objects, features and advantages of the present invention will become more apparent from a reading of the following description in connection with the accompanying drawings in which:

FIG. 2A is a graph showing the effect of ANXA1sp on NF-κB activity over time on NIH 3T3 cells activated with LPS alone and LPS+peptide. FIG. 2B is a graph showing the effect of ANXA1sp on interleukin-6 (IL-6) production over time by NIH 3T3 cells activated with LPS alone and LPS+peptide. FIG. 2C shows images of NIH 3T3 cells over time activated with LPS or LPS+peptide.

FIG. 5A is a schematic diagram of a rat cardiopulmonary bypass (CPB) apparatus and surgical preparation highlighting the aortic balloon catheter serving as an endoaortic crossclamp for initiation of cardioplegic arrest (CA). FIG. 5B is a graph showing blood glucose levels of rats in different groups. Groups were counted in a total of eight random fields in triplicate wells. Values presented are means±SD; n=8.

DETAILED DESCRIPTION OF THE INVENTION

Figure 1:
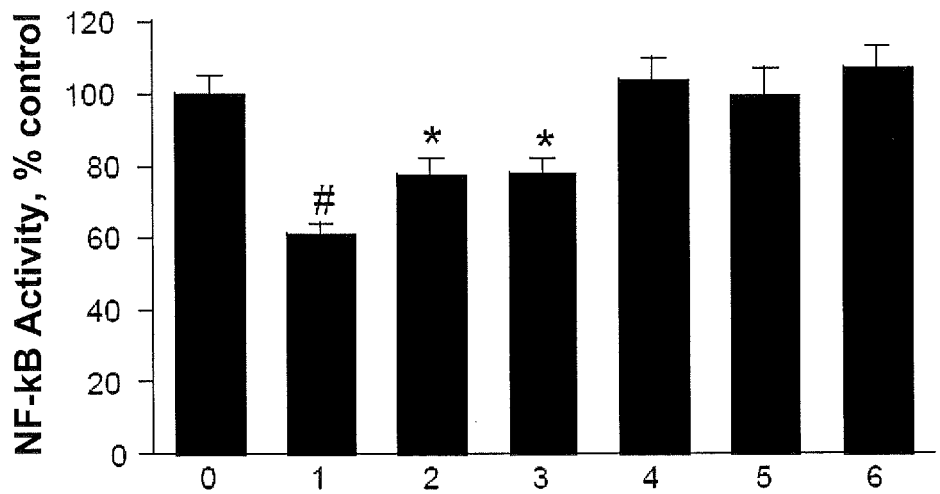
FIG. 1 is a graph showing the effect of ANXA1 N-terminus short peptides Ac-QAW, Ac-KQAW (SEQ ID NO:3), Ac-AMVSEFLKQAWFIENEEQEYVQYVK (SEQ ID NO:10), Ac-FLK, Ac-EFLKQAW (SEQ ID NO:6) and Ac-VSE-FLKQAW (SEQ ID NO:9) on NF-kB activation in human pancreatic cancer cell lines. Values presented are means±SD; n=5; *P<0.05 and #P<0.001 vs. control (0). Ac=acetylation.

The present invention is based on the surprising and unexpected discovery that ANXA1sp peptide is effective in treating and/or preventing myocardial ischemia/reperfusion injury and in treating and/or preventing perioperative myocardial injury secondary to ischemia reperfusion injury. Thus, in one embodiment, the present invention provides a method of treating myocardial ischemia/reperfusion injury in a subject (e.g., a subject in need thereof), comprising administering to the subject an effective amount of an ANXA1sp peptide.

Also provided herein is a method of ameliorating myocardial ischemia/reperfusion injury in a subject (e.g., a subject in need thereof), comprising administering to the subject an effective amount of an ANXA1sp peptide.

Further provided herein is a method of preventing myocardial ischemia/reperfusion injury in a subject (e.g., a subject in need thereof), comprising administering to the subject an effective amount of an ANXA1sp peptide.

In the methods of this invention, the myocardial ischemia/reperfusion injury can be perioperative. Thus, the condition to be treated can be perioperative myocardial injury (PMI) secondary to ischemia/reperfusion. As used herein, the term "perioperative" includes the time before (preoperative), during (intraoperative), and/or after (postoperative) surgery (e.g., cardiac surgery, transplantation surgery, etc.). Thus, it is contemplated in this invention that the ANXA1sp can be administered to a subject prior to surgery (e.g., a planned surgery) to prevent myocardial ischemia/reperfusion injury, during surgery to prevent and/or treat the onset of myocardial ischemia/reperfusion injury, and/or after surgery to prevent and/or treat myocardial ischemia/reperfusion injury. Thus, in particular embodiments, the use of the ANXA1sp peptide is planned and anticipated, in comparison with a situation in which a subject has or is at risk of having or developing myocardial ischemia/reperfusion injury associated with a heart attack or other cardiac event that was not planned or anticipated. Furthermore, targeted delivery of ANXA1sp to the myocardium via the coronary circulation is greatly facilitated by the ability to incorporate the peptide or composition into the cardioplegia solutions routinely administered during cardiac surgical operations.

It is further contemplated that in some embodiments, the subject of this invention is normoglycemic and in some embodiments the subject can be hyperglycemic, as these twins are known in the art. The data set forth in the Examples section herein demonstrates that ANXA1sp has a beneficial effect on both normoglycemic and hyperglycemic subjects.

In further embodiments, the present invention provides a kit for the treatment, amelioration and/or prevention of myocardial ischemia/reperfusion injury in a subject (e.g., a subject in need thereof), comprising ANXA1sp and instructions for use in the treatment, amelioration and/or prevention of myocardial ischemia/reperfusion injury in a subject in need thereof. In the kit of this invention, the instructions can be for use in the treatment, amelioration and/or prevention of perioperative myocardial injury secondary to ischemia/reperfusion injury.

For the purposes of promoting an understanding of the principles of the present invention, reference will now be made to various embodiments and specific language will be used to describe the same. It will nevertheless be understood that no limitation of the scope of the invention is thereby intended, such alteration and further modifications of the invention as illustrated herein, being contemplated as would normally occur to one skilled in the art to which the invention relates.

Articles "a," "an" and "the" are used herein to refer to one or to more than one (i.e., at least one) of the grammatical object of the article. By way of example, "an element" means at least one element and can include more than one element (e.g., a multiplicity or plurality of elements).

As used herein, the term "and/or" refers to and encompasses any and all possible combinations of one or more of the associated listed items, as well as the lack of combinations when interpreted in the alternative ("or").

As used herein, the term "about," when used in reference to a measurable value such as an amount of mass, dose, time, temperature, and the like, is meant to encompass variations of 20%, 10%, 5%, 1%, 0.5%, or even 0.1% of the specified amount.

As used herein, "one or more" can mean one, two, three, four, five, six, seven, eight, nine, ten or more, up to any number.

Unless otherwise defined, all technical terms used herein have the same meaning as commonly understood by one of ordinary skill in the art to which this disclosure belongs.

As used herein, the term "subject" and "patient" are used interchangeably herein and refer to both human and nonhuman animals. The term "nonhuman animals" includes all vertebrates, e.g., mammals and non-mammals, such as non-human primates, sheep, dog, pig, cat, horse, cow, chickens, amphibians, reptiles, rodents (e.g., mice, rats, etc.) and the like. In particular embodiments, the subject of this invention is a human subject.

A "subject in need thereof" or "a subject in need of" is a subject known to have, or is suspected of having or developing myocardial ischemia/reperfusion injury or is at risk of having or developing myocardial ischemia/reperfusion injury as described herein. In particular embodiments, the subject is in need of, is scheduled for and/or is planning to undergo cardiac surgery (e.g., to treat a cardiac disorder or for cardiac transplantation).

For example, in particular embodiments, a subject of this invention can be administered the peptide of this invention prior to surgery (e.g., prophylactically) to prevent perioperative myocardial injury due to ischemia/reperfusion. A subject of this invention can also be administered the peptide of this invention during and/or following surgery to prevent or treat perioperative myocardial injury due to ischemia/reperfusion. Further, the peptide can be administered to an organ donor prior to thoracic organ harvesting to improve cardioprotection/reduce myocardial injury and dysfunction in the transplanted heart, which is subject to a mandatory period of ischemia followed by reperfusion.

In certain embodiments, a subject of this invention can also include a subject not previously known or suspected to have myocardial ischemia/reperfusion injury or be in need of treatment for myocardial ischemia/reperfusion injury.

The term "administering" or "administered" as used herein is meant to include topical, parenteral and/or oral administration, all of which are described herein. Parenteral administration includes, without limitation, intravenous, subcutaneous and/or intramuscular administration (e.g., skeletal muscle or cardiac muscle administration). In the methods of this invention, the peptide of this invention may be administered alone and/or simultaneously with one or more other compounds. In some embodiments, the compounds may be administered sequentially, in any order. It will be appreciated that the actual method and order of administration will vary according to, inter alia, the particular preparation of compound(s) being utilized, and the particular formulation(s) of the one or more other compounds being utilized. The optimal method and order of administration of the compounds of the invention for a given set of conditions can be ascertained by those skilled in the art using conventional techniques and in view of the information set out herein.

The term "administering" or "administered" also refers, without limitation, to oral, sublingual, buccal, transnasal, transdennal, rectal, intramuscular, intravenous, intraarterial (intracoronary), intraventricular, intrathecal, and subcutaneous routes. In accordance with good clinical practice, the instant compounds can be administered at a dose that will produce effective beneficial effects without causing undue harmful or untoward side effects, i.e., the benefits associated with administration outweigh the detrimental effects.

Also as used herein, the terms "treat," "treating" or "treatment" refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, delay of the onset of the disease, disorder, or illness, and/or change in clinical parameters of the condition, disorder, disease or illness, etc., as would be well known in the art.

An "effective amount" or "therapeutically effective amount" refers to an amount of a compound or composition of this invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an effective amount or therapeutically effective amount in any individual case can be determined by one of ordinary skill in the art by reference to the pertinent texts and literature and/or by using routine experimentation. (See, for example, Remington, *The Science and Practice of Pharmacy* (latest edition)).

As used herein, the term "ameliorate" refers to the ability to make better, or more tolerable, a condition, disorders and/or symptom. The term "prevent" refers to the ability to keep a condition, a reaction, a disorder and/or symptom from happening or existing, as well as to delay or diminish onset.

ANXA1 has a molecular weight of about 37 kDa and consists of about 346 amino acids. The amino acid sequence is coded for by nucleotides 75-1115 of GENBANK® Database Accession number X05908 (SEQ ID NO:1) and is known by one skilled in the art as GENBANK® Database Accession number P04083 (SEQ ID NO:2). As used herein, the term "ANXA1 peptides" or "Annexin A1 peptides" are peptide fragments of annexin 1, and are shorter than ANXA1, but have similar biological effects as ANXA1 on a cell. ANXA1 peptides may optionally be acetylated (Ac-) at the N-terminal amino acid residue. ANXA1 peptides include, but are not limited to, the ANXA1sp, Ac-Gln-Ala-Trp, the peptide Ac-Lys-Gln-Ala-Trp (SEQ ID NO:3); the peptide Ac-Phe-Leu-Lys, the peptide Ac-Phe-Gln-Ala-Trp (SEQ ID NO:4), the peptide Ac-Phe-Leu-Lys-Gln-Ala-Trp (SEQ ID NO:5), the peptide Glu-Phe-Leu-Lys-Gln-Ala-Trp (SEQ ID NO:6), the peptide Phe-Gln-Ala-Trp (SEQ ID NO:4), the peptide Phe-Leu-Lys-Gln-Ala-Trp (SEQ ID NO:7), the peptide Ac-Ala-Met-Val-Ser-Glu-Phe-Leu-Lys-Gln-Ala-Trp (SEQ ID NO:8), the peptide Ala-Met-Val-Ser-Glu-Phe-Leu-Lys-Gln-Ala-Trp (SEQ ID NO:8), the peptide Ac-Val-Ser-Glu-Phe-Leu-Lys-Gln-Ala-Trp (SEQ ID NO:9) or other fragments of annexin 1 singly or in any combination, as long as they maintain the annexin 1 functionality. As used herein, the term "Ac2-26" refers to a 25mer peptide derived from annexin 1 having the sequence Ac-Ala-Met-Val-Ser-Glu-Phe-Leu-Lys-Gln-Ala-Trp-Phe-Ile-Glu-Asn-Glu-Glu-Gln-Glu-Tyr-Val-Gln-Tyr-Val-Lys (SEQ ID NO:10). As used herein, the term "ANXA1sp" or "annexin 1 short peptide" refers to the 3mer peptide derived from ANXA1 having the sequence Ac-Gln-Ala-Trp.

Pharmaceutical compositions may be prepared as medicaments to be administered in any method suitable for the subject's condition, for example, orally, parenterally (including subcutaneous, intramuscular, and intravenous), rectally, transdermally, buccally, or nasally, or may be delivered directly to the heart by injection and/or catheter, or may be delivered to the eye as a liquid solution.

A unique form of parenteral administration is via direct access to the coronary circulation, added to cardioplegia solutions routinely used during cardiac surgery. Such delivery can follow an antegrade route (via the aortic root into the coronary arteries) and/or a retrograde route (via the coronary sinus, great heart vein).

Suitable forms for oral administration include, but are not limited to, tablets, powders, compressed or coated pills, dragees, sachets, hard or gelatin capsules, sub-lingual tablets, syrups, and suspensions. Suitable forms of parenteral administration include, but are not limited to, an aqueous or non-aqueous solution or emulsion. Suitable forms for rectal administration, include, but are not limited to, suppositories with hydrophilic or hydrophobic vehicles. For topical administration, suitable forms include, but are not limited to, suitable transdermal delivery systems known in the art, such as patches, and for nasal delivery, suitable forms include, but are not limited to, aerosol and nebulized delivery systems known in the art.

In addition to the ANXA1 peptides provided herein, pharmaceutical compositions of the present invention may contain one or more excipients or adjuvants. Selection of excipients and/or adjuvants and the amounts to use may be readily determined by the formulation scientist upon experience and consideration of standard procedures and reference works in the field.

Excipients such as diluents increase the bulk of a solid pharmaceutical composition, and may make a pharmaceutical dosage form containing the composition easier for the patient and care giver to handle. Diluents for solid compositions include, but are not limited to, microcrystalline cellulose (e.g., AVICEL®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol, or talc.

Solid pharmaceutical compositions that are compacted into a dosage form, such as a tablet, may include, but are not limited to, excipients whose functions include, but are not limited to, helping to bind the active ingredient and other excipients together after compression, such as binders. Binders for solid pharmaceutical compositions include, but are not limited to, acacia, alginic acid, carbomer (e.g., CARBOPOL®), carboxymethylcellulose sodium, dextrin, ethyl cellulose, gelatin, guar gum, hydrogenated vegetable oil, hydroxyethyl cellulose, hydroxypropyl cellulose (e.g., KLUCEL®), hydroxypropyl methyl cellulose (e.g., METHOCEL®), liquid glucose, magnesium aluminum silicate, maltodextrin, methylcellulose, polymethacrylates, povidone (e.g., KOLLIDON®, PLASDONE®), pregelatinized starch, sodium alginate, or starch.

The dissolution rate of a compacted solid pharmaceutical composition in the subject's stomach may be increased by the addition of a disintegrant to the composition. Excipients which function as disintegrants include, but are not limited to, alginic acid, carboxymethylcellulose calcium, carboxymethylcellulose sodium (e.g., AC-DI-SOL®, PRIMELLOSE®), colloidal silicon dioxide, croscarmellose sodium, crospovidone (e.g., KOLLIDON®, POLYPLASDONE®), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB®), or starch.

Glidants can be added to improve the flowability of a non-compacted solid composition and to improve the accuracy of dosing. Excipients that may function as glidants include, but are not limited to, colloidal silicon dioxide, magnesium trisilicate, powdered cellulose, starch, talc, or tribasic calcium phosphate.

When a dosage form such as a tablet is made by the compaction of a powdered composition, the composition is subjected to pressure from a punch and die. Some excipients and active ingredients have a tendency to adhere to the surfaces of the punch and die, which can cause the product to have pitting and other surface irregularities. A lubricant can be added to the composition to reduce adhesion and ease the release of the product from the die. Excipients that function as lubricants include, but are not limited to, magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, or zinc stearate.

Flavoring agents and flavor enhancers make the dosage form more palatable to the patient. Common flavoring agents and flavor enhancers for pharmaceutical products that may be included in the composition of the invention include, but are not limited to, maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, the active ingredient and any other solid excipients are suspended in a liquid carrier such as water, vegetable oil, alcohol, polyethylene glycol, propylene glycol, or glycerin. As used herein, "active ingredient" means ANXA1 peptides described herein.

Liquid pharmaceutical compositions may contain emulsifying agents to disperse uniformly throughout the composition an active ingredient or other excipient that is not soluble in the liquid carrier. Emulsifying agents that may be useful in liquid compositions of the invention include, but are not limited to, gelatin, egg yolk, casein, cholesterol, acacia, tragacanth, chondrus, pectin, methyl cellulose, carbomer, cetostearyl alcohol, or cetyl alcohol.

Liquid pharmaceutical compositions of the present invention may also contain a viscosity enhancing agent to improve the mouth-feel of the product and/or coat the lining of the gastrointestinal tract. Such agents include, but are not limited to, acacia, alginic acid, bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, or xanthan gum.

Sweetening agents such as sorbitol, saccharin, sodium saccharin, sucrose, aspartame, fructose, mannitol, or invert sugar may be added to improve the taste.

Preservatives and chelating agents such as alcohol, sodium benzoate, butylated hydroxy toluene, butylated hydroxyanisole, or ethylenediamine tetraacetic acid may be added at levels safe for ingestion to improve storage stability.

According to the invention, a liquid composition may also contain a buffer such as gluconic acid, lactic acid, citric acid or acetic acid, sodium gluconate, sodium lactate, sodium citrate, or sodium acetate.

Pharmaceutical compositions of the present invention discussed above may be useful for inhibiting inflammation. "Inhibiting inflammation" also means decreasing inflammation, decreasing expression of pro-inflammatory cytokines, and/or decreasing or inhibiting the inflammation cascade.

In prophylactic applications, pharmaceutical compositions or medicaments are administered to a subject susceptible to, or otherwise at risk of, having or developing myocardial ischemia/reperfusion injury (e.g., those subjects at risk for heart attack, stroke, myocardial infarction, etc.) in an amount sufficient to eliminate or reduce the risk, lessen the severity, or delay the outset of the injury, including biochemical, histologic and/or physiologic symptoms of the injury. In particular prophylactic applications, the peptide of this invention is administered to a subject perioperatively to prevent myocardial ischemic/reperfusion injury associated with cardiac surgery or transplantation.

In therapeutic applications, compositions or medicaments are administered to a subject suspected of having, or already having such a myocardial ischemic/reperfusion injury in an amount sufficient to cure, or at least partially arrest, the symptoms of the injury (biochemical, histologic and/or physiological). An amount adequate to accomplish therapeutic or prophylactic treatment is defined as a therapeutically or prophylactically-effective dose or as an effective dose. In both prophylactic and therapeutic regimens, ANXA1 peptides of the present invention can be administered in several dosages until a desired effect has been achieved.

Effective doses of the compositions of the present invention, for the treatment of the above described conditions vary depending upon many different factors, including means or mode of administration, target site, physiological state of the subject, whether the subject is human or an animal, other medications administered, and whether treatment is prophylactic or therapeutic. Usually, the subject is a human but nonhuman mammals including transgenic mammals can also be treated. Treatment dosages can be titrated to optimize safety and efficacy. Generally, an effective amount of the agents described above will be determined by the age, weight and condition or severity of disease of the subject.

The amount of ANXA1 peptide depends on whether additional active and/or inactive compounds, such as pharmaceutical carriers, are also administered, with higher dosages being required in the absence of additional compounds. The amount of an ANXA1 peptide for administration can be from about 1 µg to about 500 µg per patient and in some embodiments can be from about 5 µg to about 500 µg per administration for human administration. In particular embodiments, a higher dose of about 1-2 mg per administration can be used. Typically about 10, 20, 50 or 100 µg is used for each human administration.

Generally, dosing may be one or more times daily, or less frequently, such as once a day, once a week, once a month, once a year, once in a decade, etc. and may be in conjunction with other compositions as described herein. In certain embodiments, the dosage is greater than about 1 µg/subject and usually greater than about 10 µg/subject if additional compounds are also administered, and greater than about 10 µg/subject and usually greater than about 100 µg/subject in the absence of additional compounds, such as a pharmaceutical carrier.

An example of a possible dosage regimen may consist of an initial administration of ANXA1 peptide prior to injury (e.g., prior to or at the beginning of surgery), intraoperative targeted coronary administration with cardioplegia solutions, followed by booster injections at selected time intervals after injury or surgery, such as 1 hour, 1 day or 1 week intervals. Another regimen may consist of an initial intraoperative targeted coronary administration with cardioplegia solutions, followed by administration of ANXA1 peptide immediately following injury (e.g., surgery), with booster injections every 1, 2 or 12 hours later. It should be noted that the present invention is not limited to the dosages recited herein.

The dosage and frequency of administration can vary depending on whether the treatment is prophylactic or therapeutic. In prophylactic applications, a relatively low dosage can be administered at relatively infrequent intervals over a long period of time. Some patients may continue to receive treatment for the rest of their lives. In therapeutic applications, a relatively high dosage at relatively short intervals is sometimes required until severity of the injury is reduced or terminated, and preferably until the subject shows partial or complete amelioration of symptoms of injury. Thereafter, the subject can be administered a prophylactic regimen.

The aforementioned embodiments are not exclusive and may be combined in whole or in part.

As will be understood by one skilled in the art, there are several embodiments and elements for each aspect of the claimed invention, and all combinations of different elements are hereby anticipated, so the specific combinations exemplified herein are not to be construed as limitations in the scope of the invention as claimed. If specific elements are removed or added to the group of elements available in a combination, then the group of elements is to be construed as having incorporated such a change.

The present invention is explained in greater detail in the following non-limiting examples.

EXAMPLES

Example 1

Determination of ANXA1sp

Annexin 1 has been shown to be an endogenous anti-inflammatory protein (Perretti and Gavins. (2003) *News Physiol. Sci.* 18:6064). In particular, it has been shown that Annexin A1 (ANXA1) peptides protect against experimental myocardial ischemia-reperfusion (see, e.g., La et al. supra). Several peptides have already been devised, such as the 25 mer Ac2-26. However, such peptides present significant research and cost hurdles. For example, and as shown in Table 1, shorter peptides are more cost efficient to produce. Therefore, it was an objective to find a smaller, effective peptide of ANXA1.

As shown in FIG. 1, several peptides were produced and tested on their ability to inhibit NF-κB activation in human pancreatic cancer cell lines. It was found that the 3 mer ANXA1sp having the amino acid sequence Ac-Gln-Ala-Trp was most effective at inhibiting NF-κB activity in these cells.

Example 2

Figure 2:
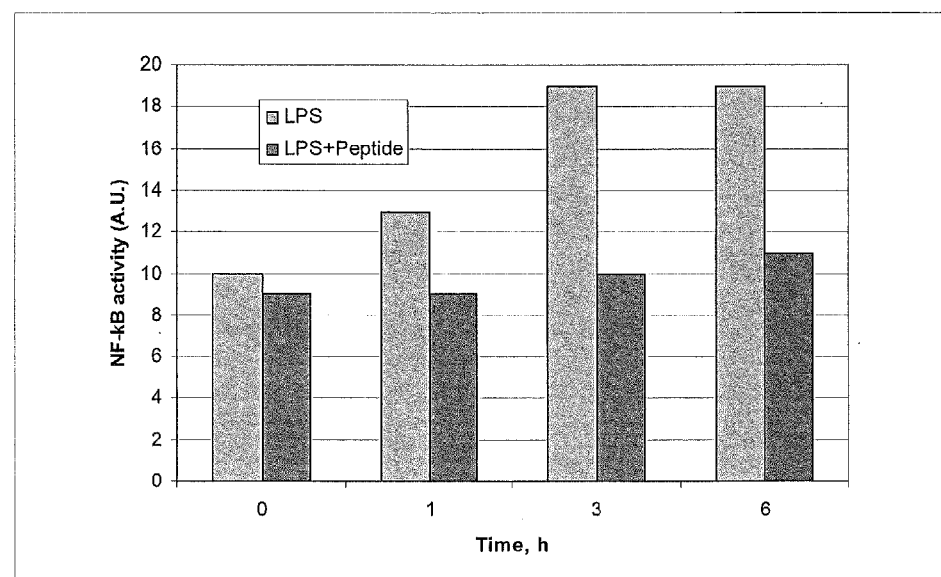
FIGS. 2A-C show results demonstrating that ANXA1sp attenuates LPS-induced NIH 3T3 cell death by inhibiting nuclear factor kappa B NF-κB proinflammatory pathways.
Figure 2:
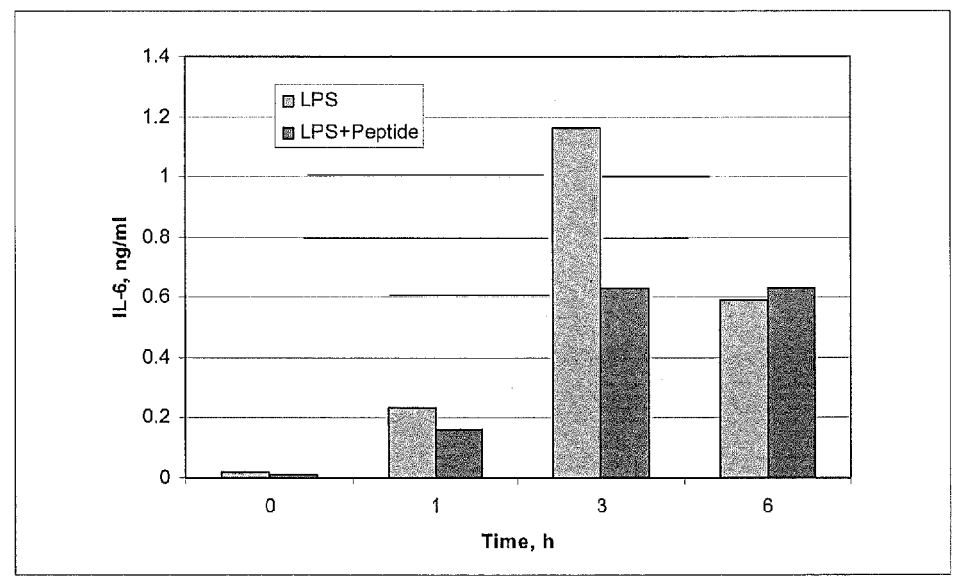
Figure 2:
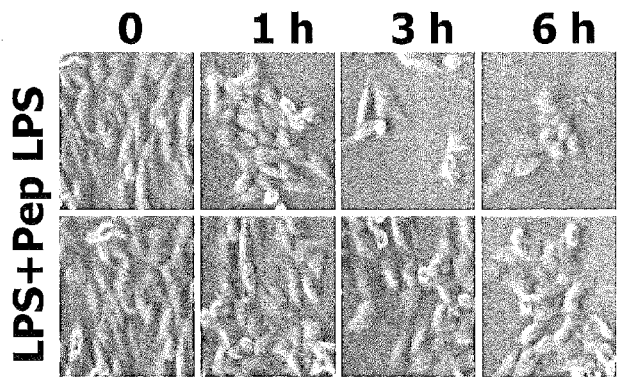

ANXA1sp Attenuates LPS-Induced NIH 3T3 Cell Death Via Inhibition of NF-κB Proinflammatory Pathways The ANXA1sp was next tested in LPS-induced NIH 3T3 cells to determine if NF-κB activity was inhibited. NIH 3T3 cells were exposed to LPS or LPS+ANXA1sp (LPS+Peptide) for 0, 1, 3 and 6 hours. Cell lysates were obtained and levels of NF-κB activity and IL-6 were measured by ELISA. Cell death was also measured by Trypan blue exclusion. As shown in FIG. 2, ANXA1sp inhibited NF-κB activity (FIG. 2A), IL-6 (FIG. 2B) and apoptosis (FIG. 2C) in NIH 3T3 cells.

Example 3

ANXA1sp Protects Cardiomyocytes from Cell Death in Vitro

Figure 3:
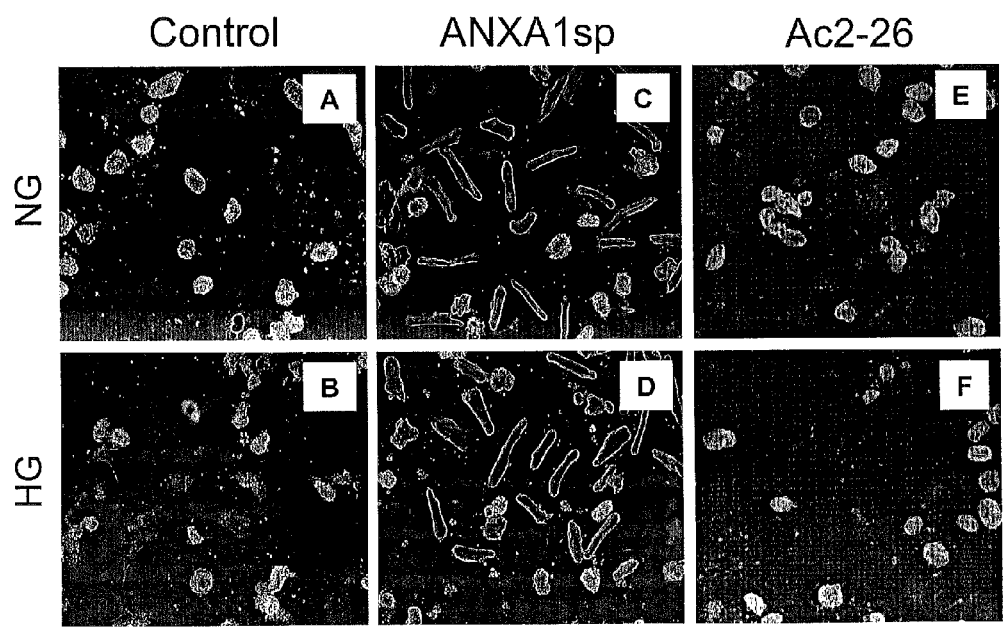
FIGS. 3A-F are images (optical microscopy) demonstrating that ANXA1sp protects adult rat ventricular cardiomyocytes (ARVC) from cell death. Cardiomyocytes isolated from adult rats were exposed to ANXAsp (FIG. 3C and FIG. 3D) or the N-terminal 25mer Ac2-26 (FIG. 3E and FIG. 3F) in either normal glucose (NG) or high glucose (HG), respectively, for 26 days. Untreated control cells in normoglycemic and hyperglycemic media are presented in FIG. 3A and FIG. 3B, FIGS. 4A-B demonstrate that ANXA1sp prevents hyperglycemic exacerbation of cell death in ARVC cells following hypoxia-reoxygenation (oxygen-glucose deprivation, OGD).
Figure 4:
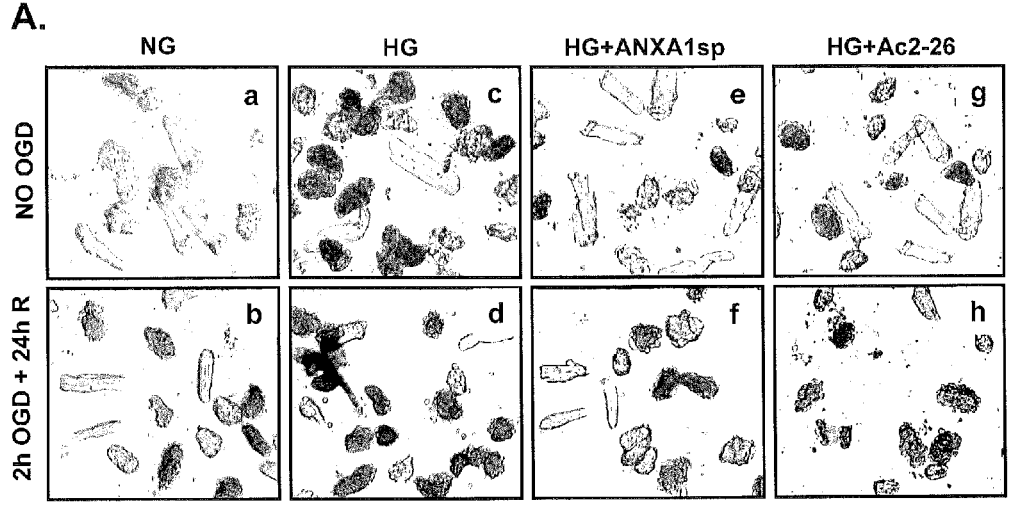
FIG. 4A. Cells were exposed to normal glucose (NG) (a, e), high glucose (HG) (b, f), HG+ANXA1sp (c, g) and HG+Ac2-26 (d, h), respectively, for 24 hours. Cells (e, f, g, h) were washed with deoxygenated glucose-free DMEM medium in an anaerobic chamber that contained a gas mixture of 5% $CO_2$, 10% $H_2$, and 85% $N_2$ and incubated for 2 hours. After oxygen/glucose deprivation (OGD), ARVC cells were cultured in DMEM medium under normoxic conditions in a 5% $CO_2$ incubator for 24 hours. Cells (a, b, c, d) without OGD were used as a control. Cell death was determined by trypan blue staining.
FIG. 4B is a graph of the results obtained in FIG. 4A. Specifically, cells were counted in a total of eight random fields in triplicate wells. Values presented are means±SD; n=8.
Figure 4:
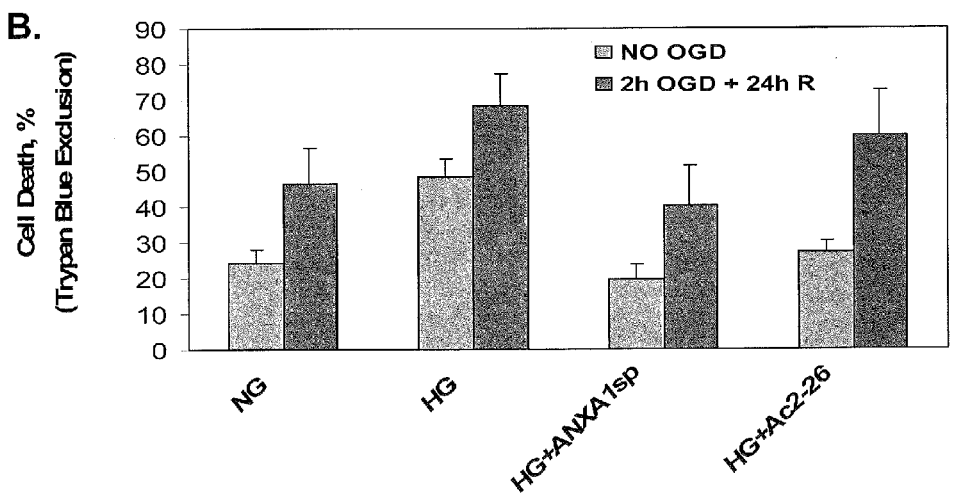

Cardiomyocytes isolated from adult rat in both normal and hyperglycemic culture media were exposed directly to ANXA1sp. As shown in FIG. 3A-F, it was found that under both normo- and hyperglycemic conditions, ANXA1sp significantly protected cardiomyocytes from cell death. Notably, this cardioprotective effect of ANXA1sp is much stronger than that of the commercial annexin A1 N-terminal peptide, Ac2-26. As shown in FIGS. 3C and 3D, at day 26, about 70% in normal glucose and 50% in high glucose of the cardiomyocytes treated with ANXA1sp were still alive, with rod-shaped morphology. However, no rod-shaped cardiomyocytes were found in either control or Ac2-26 treated cells in both normal and hyperglycemic media beyond day 14 (data not shown). The cardioprotective effects of ANXA1sp was further examined in hyperglycemic exacerbation of myocardial injury due to simulated ischemia/reperfusion in vitro. Adult rat ventricular cardiomyocytes (ARVCs) were treated with/without either ANXA1sp or Ac2-26 in both normo- and hyperglycemic culture media for 24 hours. Cells were washed with deoxygenated glucose-free DMEM medium in an anaerobic chamber that filtrated a gas mixture of 5% $CO_2$-10% $H_2$-85% $N_2$ and incubated for 2 hours. After oxygen/glucose deprivation (OGD), cells were cultured under normoxic conditions in a 5% $CO_2$ incubator for 24 hours. Cells without OGD were used as a positive control. Cell death was determined by trypan blue exclusive staining. Cells were counted in triplicate wells and in eight random fields in each well. As shown in FIG. 4, it was found that (1) OGD caused cardiomyocyte cell death (FIG. 4A: a, b); (2) hyperglycemia exacerbated cardiomyocyte cell death (FIG. 4A: c, d); (3) ANXA1sp significantly decreased cardiomyocyte cell death (FIG. 4A: e, f); and (4) ANXA1sp displayed stronger cardioprotective efficacy than Ac2-26 (FIG. 4A: e vs. g and f vs. h; FIG. 4B).

Example 4

ANXA1sp Demonstrates Cardioprotective Efficacy In Vivo

Figure 5:
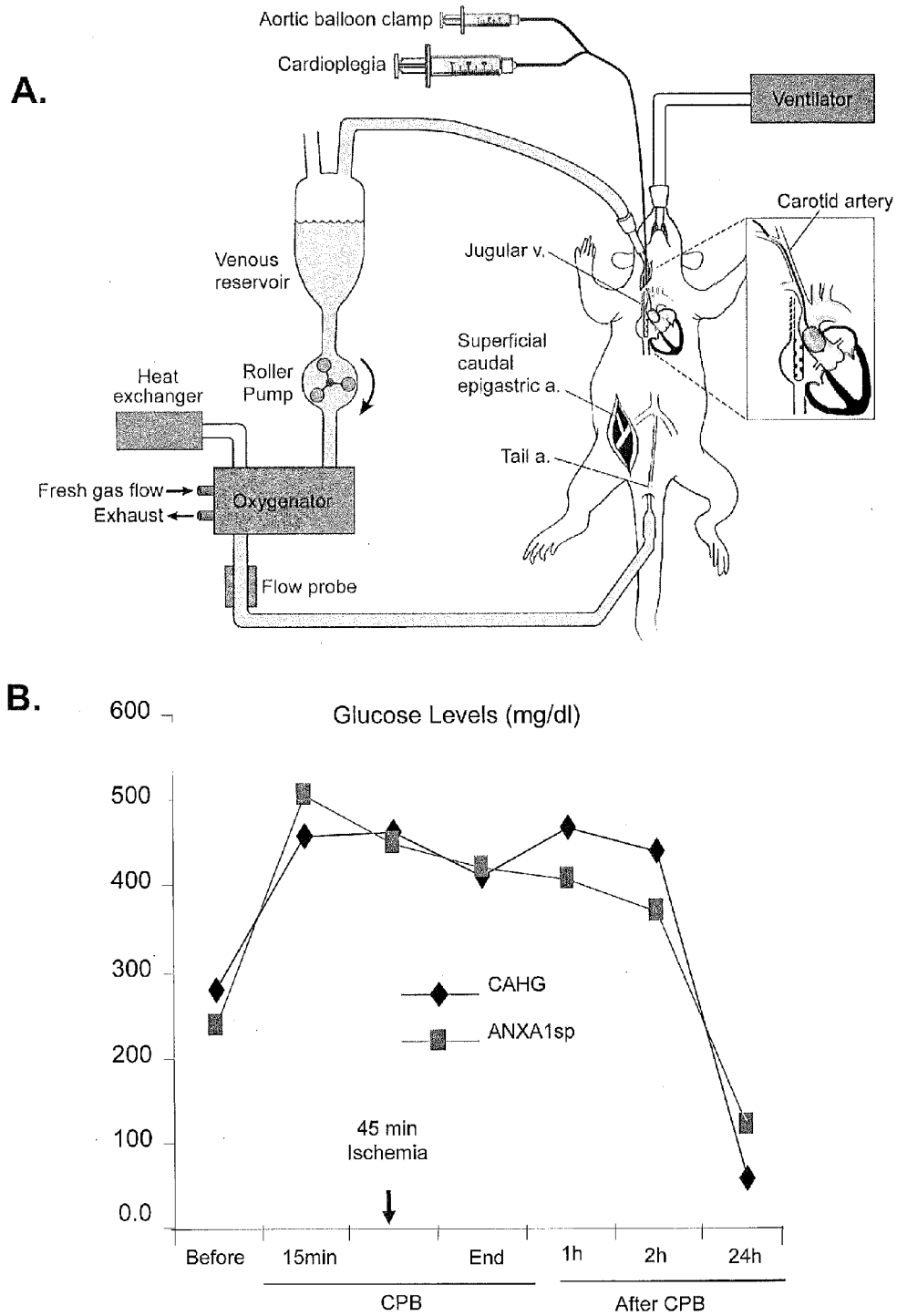
FIGS. 5A-B.

Next, studies were carried out to determine the effectiveness of ANXA1sp on myocardial protection in vivo using a clinically-relevant rodent experimental model of surgical global myocardial ischemia/reperfusion injury. As shown in FIG. 5A, open-heart surgery was performed on rats undergoing cardiopulmonary bypass (CPB), where an aortic balloon catheter was used as an endoaortic crossclamp, as previously described (de Lange et al., J Cardiothorac Surg 2008; 3:51). Rats were exposed to CPB for 15 minutes before ischemic/reperfusion injury was initiated (i.e., cardioplegic arrest was induced) and maintained for 45 minutes, followed by another 15 minutes of CPB. Animals were weaned from cardiopulmonary bypass and allowed to recover for 24 hours, at which point blood and left ventricular myocardial tissue were harvested for analysis. FIG. 5B is a graph showing the blood glucose levels in rats before and after ischemia. Acute hyperglycemia was induced using dextrose 25% (5 gm/kg) administered preoperatively 0.75 gm intraperitoneally, intraoperatively 0.25 gm in CPB prime and 0.5 gm/hr intravenously, and postoperatively 1 hour after weaning from CPB (intraperitoneally). Perioperative blood glucose levels were maintained at >300 mg/dl. Cardioplegic arrest was induced with cold (4:1) blood cardioplegia. Animals in the AXNA1sp treated group received a total of 3 mg/kg ANXA1sp in 3 equal doses administered before (intraperitoneally), during (intracoronary, mixed with cardioplegia solution), and after CPB (intraperitoneally), respectively. Control animals underwent an identical surgical procedure with vehicle instead of ANXA1sp.

Figure 6:
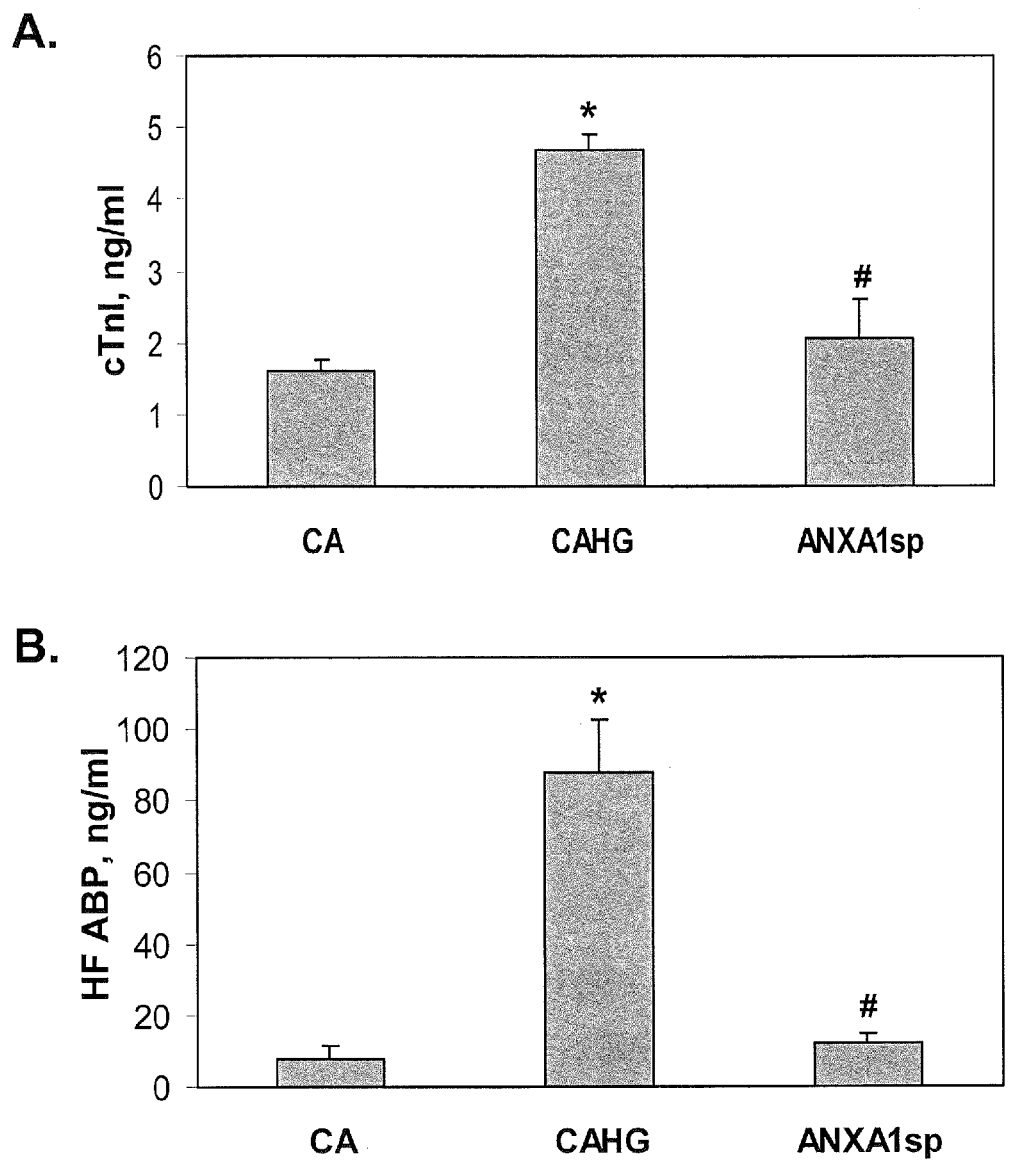
FIGS. 6A-B show that hyperglycemia significantly increases myonecrosis biomarkers cardiac Troponin I (cTnI) (FIG. 6A) and heart-type fatty acid binding protein (HFABP) (FIG. 6B), as determined by ELISA. Hyperglycemic exacerbation of myonecrosis biomarker cTnI and HFABP were attenuated by annexin 1 short peptide (ANXA1sp). Values presented are means±SD; n=3; *$P<0.01$ vs. CA; #$P<0.01$ vs. CAHG.
Figure 7:
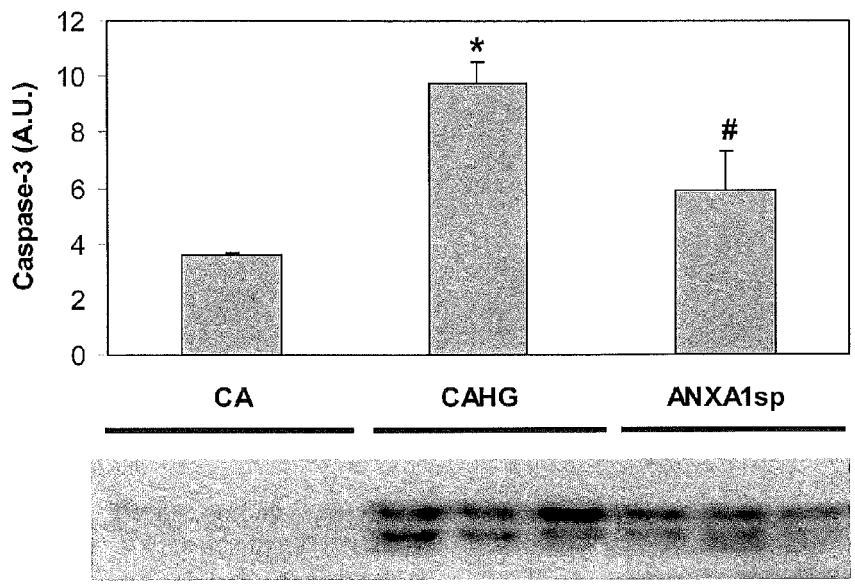
FIGS. 7A-B demonstrate that hyperglycemia increases myocardial caspase-3 activity (FIG. 7A), as determined by Western blot and apoptosis, as estimated by TUNEL staining (FIG. 7B). Hyperglycemic exacerbation of myocardial caspase-3 (FIG. 7A) and apoptosis (FIG. 7B) were attenuated by ANXA1sp. Values presented are means±SD; n=3; *$P<0.05$ vs. CA; #$P<0.05$ vs. CAHG.
Figure 7:
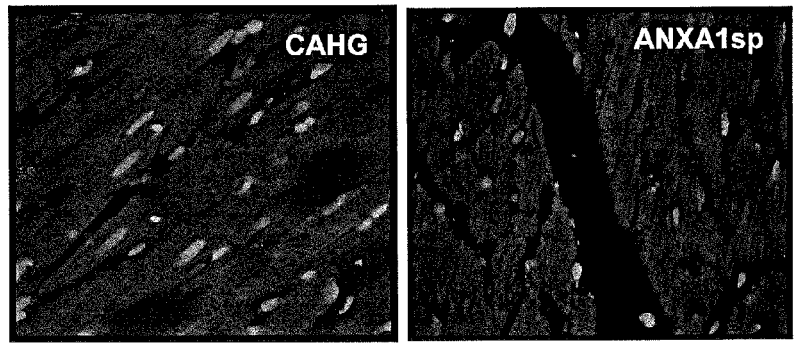
Figure 8:
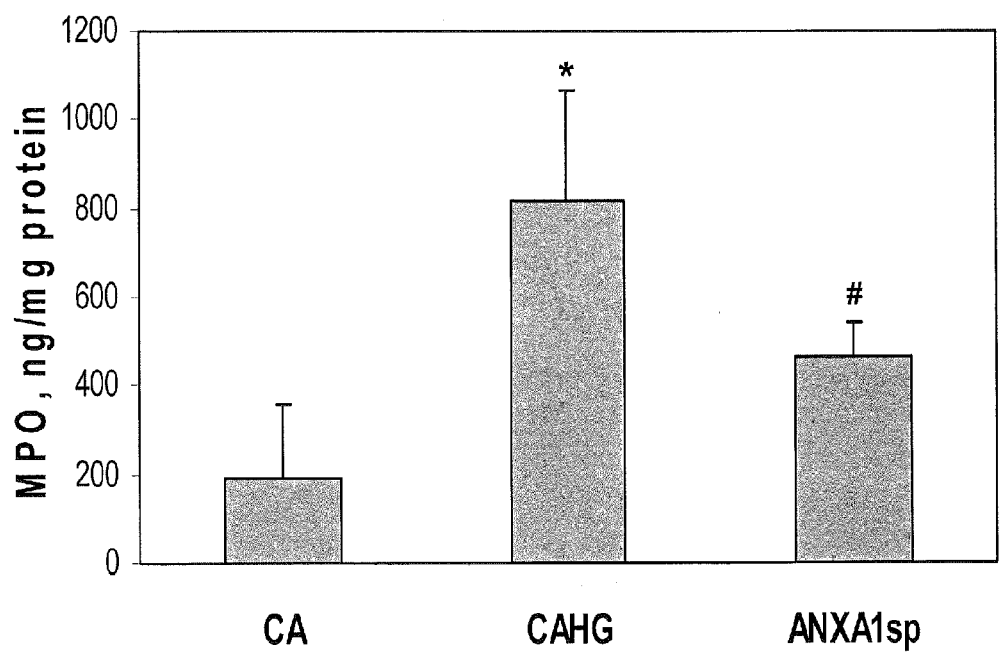
FIG. 8 is a graph showing that hyperglycemia exacerbated levels of myocardial myeloperoxidase (MPO). Hyperglycemic exacerbation of myocardial MPO was attenuated by ANXA1sp. Values presented are means±SD; n=3; *$P<0.01$ vs. CA; #$P<0.01$ vs. CAHG.
Figure 9:
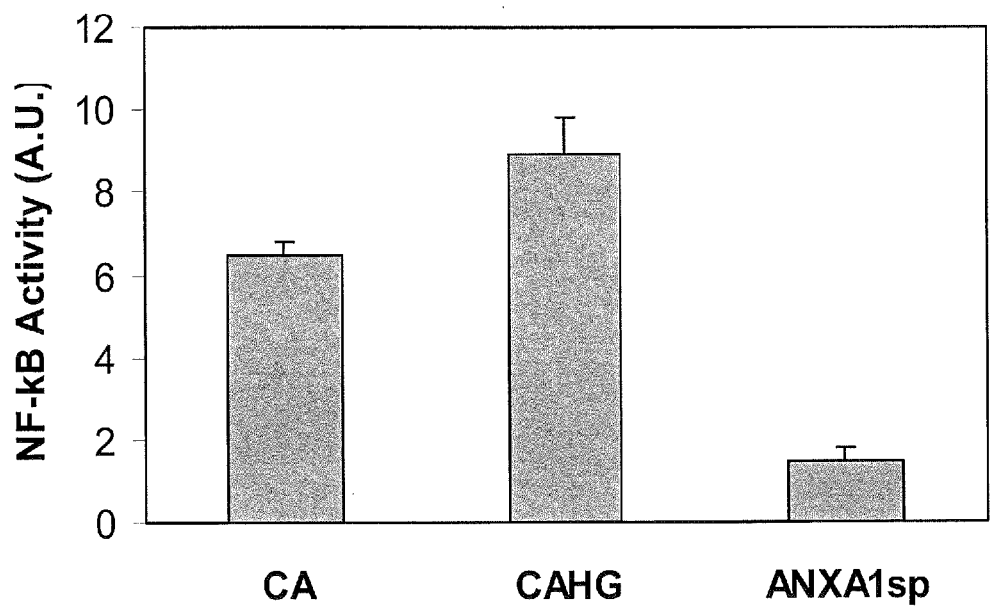
FIG. 9 show that hyperglycemia increases NF-κB DNA binding activity as determined by ELISA using myocardial nuclear proteins. Hyperglycemic exacerbation of myocardial NF-κB DNA binding activity was attenuated by ANXA1sp. Values presented are means±SD; n=3; *$P<0.05$ vs. CA; #$P<0.01$ vs. CAHG.
Figure 10:
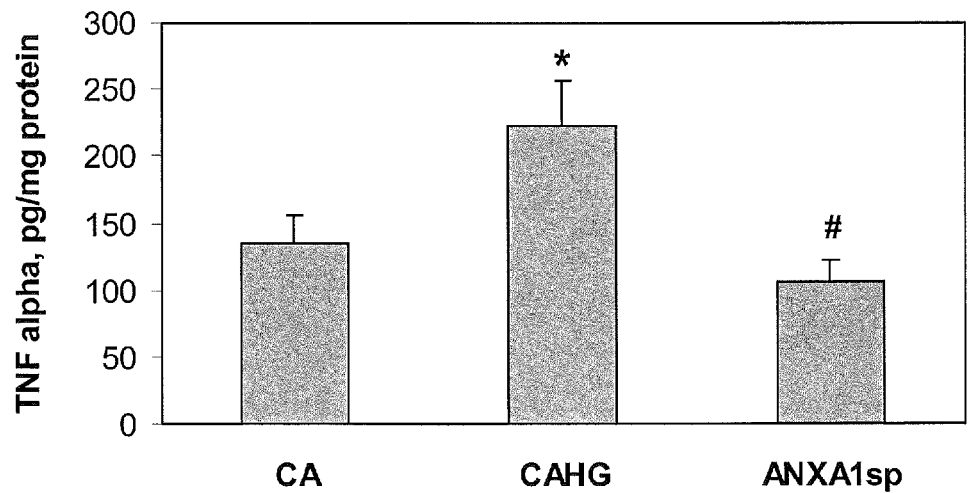
FIGS. 10A-B show that hyperglycemia significantly increases myocardial proinflammatory cytokines such as TNF-α (FIG. 10A) and IL-6 (FIG. 10B), as measured by ELISA. Hyperglycemic exacerbation of myocardial proinflammatory cytokines TNF-α (FIG. 10A) and IL-6 (FIG. 10B) were attenuated by ANXA1sp. Values presented are means±SD; n=3; *$P<0.05$ vs. CA; #$P<0.05$ vs. CAHG.
Figure 10:
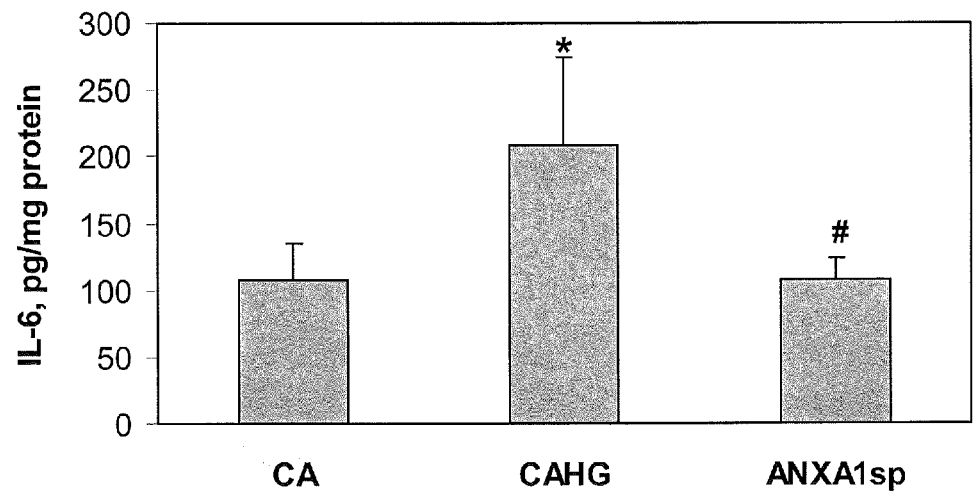
Figure 11:
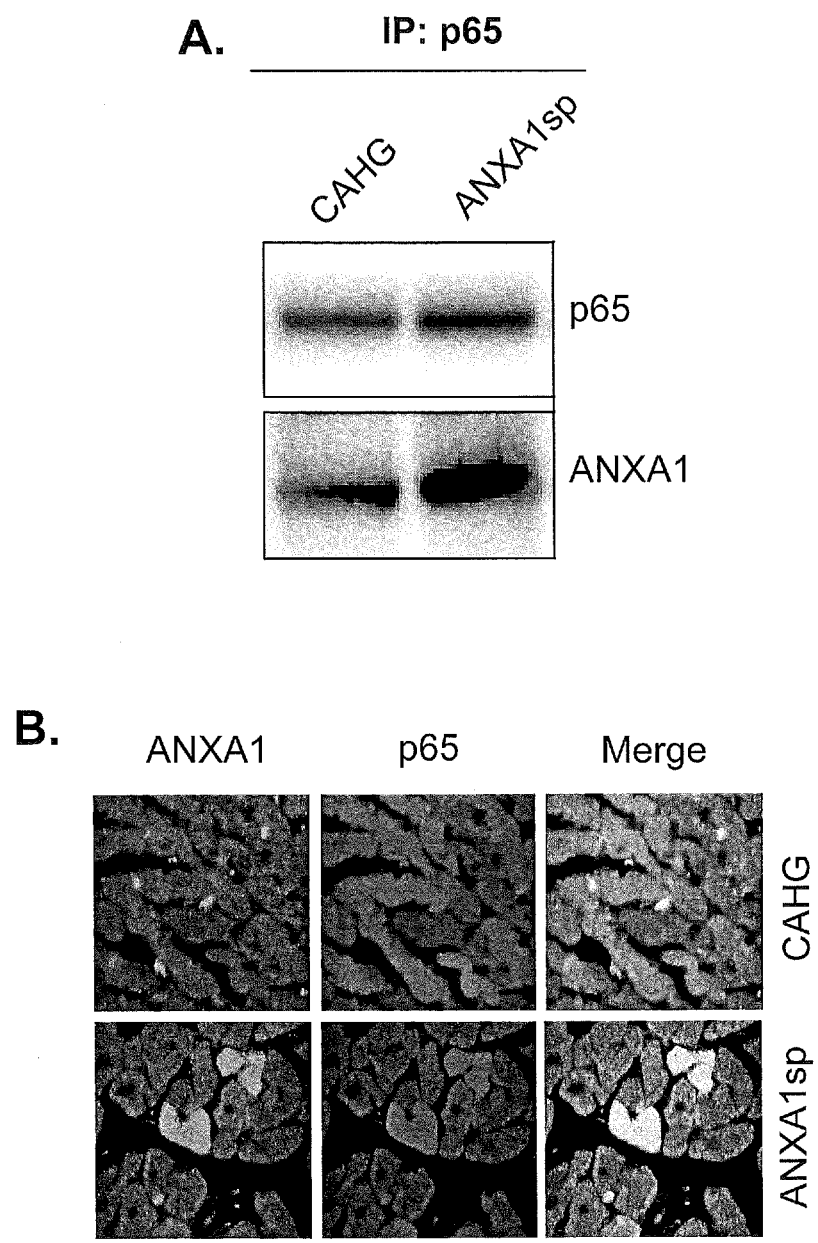
FIGS. 11A-B show that ANXA1sp significantly induces in vivo interactions between ANXA1 and NF-ΛB p65 as determined by co-immunoprecipitation (FIG. 11A) and confocal co-localization microscopy (FIG. 11B) in cardiomyocytes. ANXA1 is shown in the left panel; p65 is shown in the center panel; and the co-localization between ANXA1 and p65 is shown in the right panel.

In a rodent model of global myocardial ischemia-reperfusion injury associated with cardioplegic arrest and acute hyperglycemia, administration of ANXA1sp (3 mg/kg) attenuated hyperglycemic exacerbation of perioperative myocardial injury. Specifically, ANXA1sp significantly decreased levels of myonecrosis biomarkers cTnI (FIG. 6A) and HFABP (FIG. 6B), myocardial caspase-3 activity (FIG. 7A) and apoptosis (FIG. 7B), MPO (FIG. 8), NF-κB activity (FIG. 9), and pro-inflammatory cytokines TNF-α (FIG. 10A) and IL-6 (FIG. 10B). ANXA1sp also strongly induced the in vivo interaction between ANXA1 and NF-κB p65 subunit, as evidenced by co-immunoprecipitation (FIG. 11A) and co-localization between the two of them (FIG. 11B).

In a porcine model of cardioplegic arrest, administration of ANXA1sp (4 mg/kg, systemically and in the cardioplegia solution) resulted in significant reduction in postoperative arrhythmias, left ventricular dysfunction and vasoplegia as evidenced by the need for inotropic and vasopressor support.

These findings facilitate the first-in-human studies for ANXA1sp to reduce myocardial injury in patients undergoing cardiac surgery. This short peptide is a potential agent/therapy for perioperative/periprocedural cardioprotection, as an adjunct to reperfusion therapy in acute coronary syndromes as well as other areas, such as perioperative neuroprotection, transplantation, and other disorders associated with neutrophil-mediated ischemia-reperfusion injury (e.g., major trauma, hemorrhagic shock, crush injury, stroke, myocardial infarctions, etc.).

Example 5

Further Studies In Vitro and In Vivo

Despite improvements in operative mortality, serious cardiovascular complications including perioperative myocardial injury (PMI) secondary to ischemia-reperfusion (I/R) continue to limit the benefits of cardiac surgical procedures. Several promising small proof-of-concept clinical studies on cardioprotection were followed by failures in phase-3 RCTs, underscoring that translation of experimental cardioprotective strategies into clinical therapy remains an unmet clinical need.

Several preclinical translational barriers specifically addressed in this study include using inadequate animal models that do not approximate the clinical setting, lack of emphasis on efficacy, and insufficient survival periods after I/R.

Further, acute hyperglycemia (AHG), a risk factor for hospital mortality and morbidity following acute ischemic events and a common occurrence during cardiac surgery, is known to not only exacerbate PMI but also blunt the few existing perioperative cardioprotective therapies (e.g., preconditioning).

Anti-inflammatory properties have been identified in a short peptide derived from the N-terminal domain of Annexin-A1 (ANXA1sp) and its cardioprotective properties have been studied in several in vitro and in vivo preclinical models of myocardial I/R injury under both eu- and hyperglycemic conditions. In addition, it has been demonstrated that the observed cardioprotective effects of ANXA1sp are through the inhibition of NF-κB activation, expression of pro-inflammatory genes such as cytokines, attenuation of neutrophil transmigration, and in turn, decrease in myocardial necrosis and apoptosis.

I. Model of Cultured Cardiomyocytes Simulated I/R Injury.

In vitro study: ARVCs from male Sprague-Dawley (SD) rats were incubated in normal or high glucose (25 mM), with and without 30 μM ANXA1sp (Ac-QAW), or with a scrambled peptide (Ac-QWA), respectively for 24 h. Cells were subjected to 2 h oxygen-glucose deprivation (OGD), followed by 24 h reoxygenation in either normo- or hyperglycemic conditions. Cell death was determined histologically (trypan blue exclusion) and biochemically (supernatant levels of cTnI and HFABP, ELISA). Apoptosis was quantified using ELISA (Roche).

II. Rat Model of Myocardial I/R Injury.

In vivo study: with IACUC approval, male SD rats were randomly assigned to 4 groups in a 2×2 design (n=5/group): normo- and hyperglycemic (20 mM) cardioplegic arrest (CA), each treated with ANXA1sp or vehicle, respectively. All animals underwent 75 min of mild hypothermic CPB (33° C.) with 45 min of CA using blood cardioplegia. Treatment groups received ANXA1sp (Ac-QAW, GenScript, 3 mg/kg total) before (ip), during (with cardioplegia), and after CPB (ip) in equal doses, whereas CA control animals received saline. No animals received insulin. At 24 h post-reperfusion the following efficacy end-points were assessed by investigators blinded to the experimental group: 1) plasma myonecrosis biomarkers—cTnI and HFABP (rat specific ELISA, Life-Diagnostics); 2) myocardial apoptosis—cleaved caspase-3 (immunostaining and Western blot) and TUNEL assays; 3) myocardial inflammation—NF-kB DNA binding activity (ELISA, Panomics) and tissue levels of TNF-α and IL-6 (ELISA, ThermoScientific); and 4) myocardial neutrophil transmigration—myeloperoxidase (MPO) activity (ELISA, ThermoScientific).

III. Pig Model of Myocardial I/R Injury.

Pig CPB/CA: Male Yorkshire pigs (32-38 kg) were subjected to 120 min of mild hypothermic CPB, including 60 min of CA using 4:1 blood cardioplegia, and received either ANXA1sp (iv after anesthesia induction and with each dose of cardioplegia, 4 mg/kg total, CA_SP group, n=4) or vehicle (CA_CTRL, n=8). Efficacy endpoints and underlying mechanisms were assessed as described herein.

Results.

Acute hyperglycemia directly increased myocardial injury following I/R both in vitro and in vivo. ANXA1sp significantly attenuated myocardial I/R injury under both normo- and hyperglycemic conditions (Table 2). ANXA1sp treated pigs further demonstrated improved myocardial energetics (higher ATP levels) and improved hemodynamics, none requiring either inotropic or vasopressor support, which was substantial in all control animals (Table 2).

Using a translational approach and robust efficacy endpoints, it is demonstrated that ANXA1sp elicits cardioprotection in vitro and in clinically relevant small and large animal models of surgical I/R under both normo- and hyperglycemic conditions through attenuation of myocardial NF-κB regulated pathways and leukocyte transmigration. These studies indicate that ANXA1sp represents a suitable candidate for cardioprotection.

IV. Rat Model of Cardiopulmonary Bypass (CPB)/CA.

With IACUC approval, male SD rats were randomly assigned to 3 groups (n=7/group): CA), DHCA, and DHCASP. All animals for CA model underwent 75 min of mild hypothermic cardiopulmonary bypass (CPB, 33° C.) with 45 min of CA using blood cardioplegia, and received saline before (ip), during (with cardioplegia), and after CPB (ip).

Rat CPB/DHCA:

Male SD rats underwent CPB with 60 min of DHCA at 18 C and received either vehicle (n=7) or ANXA1sp treatment of 1 hour before CPB (ip) and 1 hour after reperfusion (ip) (total of 2 mg/kg, n=7).

Blood and heart tissue samples were harvested at 24 h post-reperfusion. Serum levels of myonecrosis biomarkers cardiac Troponin I (cTnI), heart-type fatty acid binding protein (HFABP), and myocardial tissue levels of pro-inflammatory cytokine tumor necrosis factor alpha (TNF-α) were determined by ELISA. Myocardial levels of cleaved caspase-3 were measured by Western blot while apoptotic myocytes were assayed by TUNEL staining.

Results.

In the rodent models, DHCA for 60 min without cardioplegia resulted in less myocardial injury compared to cardioplegic arrest (CA) for 45 min using cold blood cardioplegia (Table 3). ANXA1sp further attenuated myocardial I/R injury following CPB/DHCA, as evidenced by significantly reduced cTnI, HFABP, caspase-3 activity, and number of apoptotic myocardial cells. The effects were associated with a down-regulation of TNF-α in the myocardium (Table 3).

Systemically administered ANXA1sp reduced myocardial I/R injury following CPB/DHCA, thus augmenting the known robust cytoprotective effects of hypothermia. In addition to validating previous work in a different model of global surgical myocardial I/R, these results indicate that the ANXA1 peptide mimetic retains its pharmacological cardioprotective efficacy under conditions of deep hypothermia and has potential implications for organ preservation during transplantation and therapeutic hypothermia following cardiac arrest.

Example 6

Assessment of In Vivo Efficacy of ANXAsp1 for Perioperative Cardioprotection in Rat and Pig Models of Cardiac Surgery with Cardioplegic Arrest Dose Finding Studies to Determine Biological Dose and Optimal Timing of Administration of ANXA1sp in a Rat Model of CPB/CA. Non-GLP dose finding studies will be performed in male SD rats (10-12 weeks, 400-500 g) assigned to 12 groups (4 doses×3 dosing regimen time points, n=7/group). The experimental protocol for surgical preparation, conduct of CPB and CA, and efficacy endpoints will be as described herein. The design utilizes the intended route of administration in humans, with dosing regimens tested mimicking timing of perioperative drug administration the morning of surgery, while also testing the therapeutic window of a single intraoperative dose (intracoronary) mixed with cardioplegia induction solution, which also maximizes agent delivery to the intended site. Animals will be acutely dosed either 1') 4 h preoperatively (ip)+ with cardioplegia, 2) 1 h preoperatively (ip)+ with cardioplegia, or 3) with cardioplegia only, for each of the following: low (0.5 mg/kg), intermediate (6 mg/kg), and high (12 mg/kg) doses of ANXA1sp and a vehicle control group. At 24 hrs, animals will undergo comprehensive echocardiographic examination (2D and tissue Doppler indices of ventricular function) and will be sacrificed. Myocardial tissue and blood samples will be collected and processed for the proposed efficacy timepoints. In parallel, pharmacodynamic studies will be conducted to characterize the primary mode of action responsible for the observed cardioprotective effects of ANXA1sp.

Establishment of Cardioprotective Efficacy of ANXA1sp in a Pig Model of CPB/CA.

Male Yorkshire pigs (12-14 months, 40-50 kg, N=5) will be used to validate the cardioprotective effects of ANXA1sp based on the optimal dose and time determined in rats above. The experimental protocol and efficacy timepoints will be conducted as described herein. Banked myocardial tissue and plasma samples from ongoing CPB/CA experiments in pigs will be used as controls.

Preclinical Toxicity Studies in Rats.

A non-GLP escalating dose range finding study to determine maximum tolerated dose (MTD) in a single, acute administration of ANXAsp1 will be completed using SD rats. The acute MTD provides a starting point to select doses for repeated dosing MTD and for toxicology studies.

Single Dose Acute Toxicity.

Five rats of each sex will be assigned to each of six treatment groups—a single dose of ANXA1sp (ip) 0.5, 3, 6, 13, 14 mg/kg, or vehicle control. Animals will be observed daily for 14 days for signs of toxicity (e.g., progressive loss of weight, inhibition of growth, changes in food consumption or behavior, lethargy, sluggish movements). At the end of the observation period, rats of the study (e.g., rats that die during the study) will undergo a gross necropsy examination and hematology, clinical chemistry and histopathology data will be evaluated (control and high-dose only if no treatment-related pathology is seen at the high dose). If no evidence of toxicity is achieved with the highest dose, an additional experimental group will be added with a single dose of 36 mg/kg.

Repeat Dose Toxicity.

SD rats of each gender will receive one dose of ANXA1sp daily for 7 consecutive days in 4 treatment groups (low, intermediate, high, vehicle; N=3/sex/group). The exact dosage for each group will depend on the results from the acute dose studies and will be continued for 30 days after the last treatment. Ophthalmologic examinations, and hematologic and serum chemistry investigations will be performed, followed by post-mortem histopathologic examination of all tissues. The duration of repeat-dose toxicity studies is based on the 30-day duration of the majority of clinical trials of perioperative cardioprotection.

From the foregoing description, it will be apparent that an improved confocal microscopy system, tissue culturing system and methods of using same has been provided. Variations and modifications of the herein described systems, apparatuses, methods and other applications will undoubtedly suggest themselves to those skilled in the art. Accordingly, the foregoing description should be taken as illustrative and not in a limiting sense.

Any patents, patent publications and non-patent publications mentioned in this specification are indicative of the level of those skilled in the art to which the invention pertains. These patents and publications are herein incorporated by reference to the same extent as if each individual patent or publication was specifically and individually indicated to be incorporated by reference.

TABLE 1

| Synthesis* | Time (Weeks) | Fee ($) | Purity (%) |
|---|---|---|---|
| ANXA1sp (3 aa) | 2 | 295 | >98 |
| Ac2-26 (25 aa) | 6-8 | 5,757 | ~95 |

*Provided by GenScript

TABLE 2

Cardioprotective Effects of ANXA1 Short Peptide (ANXA1sp)

| | ARVC Simulated I/R | | | |
|---|---|---|---|---|
| | NG_CTRL | NG_SP | HG_CTRL | HG_SP |
| cTnI (ng/ml) | 7.3 ± 0.6 | 5.7 ± 0.4** | 14.3 ± 1.7** | 7.8 ± 0.6## |
| HFABP (ng/ml) | 3.6 ± 0.4 | 2.4 ± 1.4** | 4.0 ± 0.4* | 2.0 ± 0.4## |
| Apoptosis (A.U.) | 1.8 ± 0.2 | 0.7 ± 0.2** | 2.3 ± 0.1* | 0.7 ± 0.2# |
| Cell Death (%) | 46.6 ± 9.9 | 38.6 ± 5.9** | 68.3 ± 9.0** | 40.5 ± 11.1## |
| NF-kB Activity (A.U.) | 1.2 ± 0.08 | 1.0 ± 0.05* | 1.7 ± 0.1* | 1.4 ± 0.08# |
| TNFα (ng/mg protein) | 1.0 ± 0.1 | 0.84 ± 0.1* | 1.7 ± 0.1** | 1.2 ± 0.1## |

| | Rat CPB/CA | | | |
|---|---|---|---|---|
| | CA_CTRL | CA_SP | CAHG_CTRL | CAHG_SP |
| cTnI (ng/ml) | 2.8 ± 1.0 | 1.0 ± 0.7** | 4.7 ± 0.2* | 2.1 ± 0.5## |
| HFABP (ng/ml) | 2.5 ± 0.5 | 1.0 ± 0.3** | 87.7 ± 15.0** | 12.4 ± 2.6## |
| Caspase-3 (A.U.) | 4.1 ± 1.0 | 1.9 ± 1.5* | 9.8 ± 0.8* | 5.9 ± 1.4# |
| Apoptosis (%) | 6.3 ± 2.3 | 2.4 ± 1.1* | 24.7 ± 1.7** | 9.5 ± 1.2## |
| NF-κB activity (A.U.) | 1.4 ± 0.05 | 0.8 ± 0.04* | 8.9 ± 0.9 | 1.5 ± 0.5## |

TABLE 2-continued

| Cardioprotective Effects of ANXA1 Short Peptide (ANXA1sp) | | | | |
|---|---|---|---|---|
| TNF-α (ng/mg) | 48.6 ± 5.8 | 28.8 ± 6.7** | 223.3 ± 44.8** | 105.6 ± 13.3## |
| IL-6 (ng/mg) | 58.4 ± 6.6 | 38.2 ± 8.1* | 209.0 ± 65.0** | 107.3 ± 15.5# |
| MPO (ng/mg) | 160.0 ± 60.6 | 104.8 ± 6.6* | 818.6 ± 246.8** | 467.2 ± 72.4# |

| | Pig CPB/CA | |
|---|---|---|
| | CA_CTRL | CA_SP |
| Caspase-3 (A.U.) | 162. ± 25.1 | 137.3 ± 9.8* |
| Apoptosis (%) | 20.0 ± 6.9 | 5.9 ± 2.3** |
| ATP (μM/mg protein) | 474.6 ± 223.3 | 933.1 ± 380.7* |
| Epinephrine (mcg/6 hs) | 553.6 ± 191.3 | 0** |
| Vasopressin (U/6 hrs) | 11.4 ± 0.05 | 0** |
| Heart Rate (beats/min) | 153 ± 13 | 135 ± 18** |
| SVI (ml/m$^2$) | 32 ± 6 | 36 ± 5* |
| NF-κB activity (A.U.) | 1.4 ± 0.05 | 0.8 ± 0.04* |
| TNF-α (ng/mg protein) | 48.6 ± 5.8 | 28.8 ± 6.7** |

Results are presented as mean ± SD.
*$P < 0.05$;
**$P < 0.01$ vs. CA or NG;
$P < 0.05$;
$P < 0.01$ vs. HG or
ARVC—adult rat ventricular cardiomyocytes;
NG—normoglycemia;
HG—hyperglycemia;
CTRL—vehicle control group;
SP-ANXA1sp treated group;
CPB—cardiopulmonary bypass;
CA—cardioplegic arrest;
cTnI—troponin I;
HFABP—heart fatty acid binding protein;
MPO—myeloperoxidase;
SVI—stroke volume index;

TABLE 3

| ANXA1sp attenuates myocardial injury following DHCA in rat | | | |
|---|---|---|---|
| | CA | DHCA | DHCASP |
| cTnI (ng/ml) | 2.8 ± 1.0 | 1.8 ± 0.7* | 0.5 ± 0.3## |
| HFABP (ng/ml) | 2.5 ± 0.5 | 1.5 ± 1.2* | 0.5 ± 0.3# |
| Caspase-3 (A.U.) | 4.1 ± 1.0 | 3.9 ± 0.6** | 2.9 ± 0.6# |
| Apoptosis (%) | 6.3 ± 2.3 | 6.9 ± 3.0* | 3.3 ± 1.2# |
| TNFα (ng/mg) | 48.6 ± 5.8 | 14.9 ± 5.8** | 10.9 ± 1.7## |

Results are presented as means ± SD, n = 7.
*$P < 0.05$ &
**$P < 0.01$ vs. CA;
$P < 0.05$ and
$P < 0.01$ vs. DHCA. SP-ANXA1sp.

What is claimed is:

1. A method of treating and/or ameliorating surgical, global myocardial ischemia/reperfusion injury due to cardiac surgery or cardiac transplantation in a subject having cardiac surgery or cardiac transplantation, comprising administering to said subject an effective amount of an annexin A1 short peptide (ANXA1sp) consisting of the amino acid sequence Ac-Gln-Ala-Trp, wherein the ANXA1sp is administered to the subject prior to during, and/or after cardiac surgery or cardiac transplantation, thereby treating and/or ameliorating the surgical, global myocardial ischemia/reperfusion injury due to cardiac surgery or cardiac transplantation in the subject.

2. The method of claim 1, wherein the subject is normoglycemic.

3. The method of claim 1, wherein the subject is hyperglycemic.

* * * * *

UNITED STATES PATENT AND TRADEMARK OFFICE
CERTIFICATE OF CORRECTION

PATENT NO. : 8,940,697 B2
APPLICATION NO. : 13/502219
DATED : January 27, 2015
INVENTOR(S) : Podgoreanu et al.

Page 1 of 1

It is certified that error appears in the above-identified patent and that said Letters Patent is hereby corrected as shown below:

In the Specification:
Column 3, Line 65: Please correct "and NF-ΛB p65"
to read -- and NF-κB p65 --

In the Claims:
Column 18, Claim 1, Line 41: Please correct "subject prior to during,"
to read -- subject prior to, during, --

Signed and Sealed this
Twenty-first Day of July, 2015

Michelle K. Lee
*Director of the United States Patent and Trademark Office*